United States Patent [19]

Arnold et al.

[11] Patent Number: 4,528,406

[45] Date of Patent: Jul. 9, 1985

[54] PRODUCTION OF BIS(ALPHA-ALKYLBENZYL)ETHERS

[75] Inventors: Mary T. Arnold, Upland; George R. Siciliano, West Chester, both of Pa.

[73] Assignee: Atlantic Richfield Company, Los Angeles, Calif.

[21] Appl. No.: 556,505

[22] Filed: Nov. 30, 1983

[51] Int. Cl.$^3$ .............................................. C07C 41/09
[52] U.S. Cl. ..................... 568/659; 568/583; 568/661; 260/505 C
[58] Field of Search ............... 568/698, 659, 661, 583; 260/505 C

[56] References Cited

U.S. PATENT DOCUMENTS

| | | | |
|---|---|---|---|
| 2,366,203 | 1/1945 | Livak | 568/661 |
| 2,927,064 | 3/1960 | Luzader et al. | 568/659 X |
| 3,267,156 | 8/1966 | Hansen | 568/698 |
| 3,769,351 | 10/1973 | Mukai | 568/659 |

OTHER PUBLICATIONS

Mikhalev et al., Chem. Abs., vol. 55, (1961), 3524.

*Primary Examiner*—Bernard Helfin
*Attorney, Agent, or Firm*—Michael S. Jarosz

[57] ABSTRACT

Production of bis(alpha-alkylbenzyl)ethers or substituted derivatives thereof by reaction at elevated temperature of the corresponding alpha alkylbenzyl alcohols in the presence of a particular acidic clay catalyst, quenching of the catalyst and recovery of the desired ether by distillation directly from the reaction mixture containing the quenched catalyst, is disclosed. The alkyl methylbenzyl alcohol may be present as a component of an aromatic rich distilland product mixture derived from the ethyl benzene hydroperoxide epoxidation of an olefinically unsaturated compound.

11 Claims, No Drawings

PRODUCTION OF BIS(ALPHA-ALKYLBENZYL)ETHERS

FIELD OF THE INVENTION

This invention relates to a process for the production of bis(alpha-alkylbenzyl) ethers, such as bis(alpha-methylbenzyl) ether, by heating an alpha-alkylbenzyl alcohol, illustratively, alpha-methylbenzyl alcohol, ("MBA"), in the presence of a highly acidic clay catalyst having a surface area of at least about 100 square meters per gram. The present application is especially concerned with the use of specified acid clay catalysts in the etherification of an alpha methylbenzyl alcohol which is produced as a component of an epoxidation reaction product mixture obtained from the process for the production of an oxirane compound by the oxidation of ethylbenzene to produce an ethylbenzene hydroperoxide product mixture, followed by epoxidation of an olefinically unsaturated compound with said ethylbenzene hydroperoxide product mixture.

DESCRIPTION OF THE PRIOR ART AND BACKGROUND OF THE INVENTION

Bis(alpha-alkylbenzyl) ethers, such as bis(alpha-methylbenzyl) ether, have found application as dye carriers in the fabric industry, solvents in copying paper, and as direct substitutes for polychlorinated biphenyls in capacitors, and as heat transfer media, as well as components for use in the fragrance field. Certain of such ethers have also found use as pesticides, antioxidants, plastic additives and germicides. For example, Japanese Pat. No. 79-149900 has recently referred to the use of such ethers as electrical insulating oils and Japanese Pat. No. 79-136915 has referred to the use of such ethers in pressure-sensitive copying papers. The preparation of bis(alpha-alkylbenzyl) ethers by reaction of a suitable alpha-unsubstituted or substituted phenyl-alkanol in the presence of a dehydrating agent, such as sulfuric acid, benzene-sulfonic acid, toluene sulfonic acid, and camphor-sulfonic acid, thereby splitting out water and forming an ether linkage between the aliphatic carbon atoms of two molecules of the original alkanol compound has been reported in the literature, for example, in U.S. Pat. No. 2,366,203 and *Journal of Organic Chemistry*, 28, 2914-5 (1963). More recently, acidified alumina catalysts and ion exchange resins containing acidic functionalities have been suggested for use in the preparation of such ethers from the corresponding alkanols. However, these catalysts, as well as those originally reported for use in the etherification reaction, suffer a combination of shortcomings, including poor selectivity to the desired bis ether, poor reproducibility of results and high costs. In addition, it was necessary to employ such acid catalysts at high levels to be effective, thereby further increasing their costs, and to quench the catalyst quickly to avoid alteration of desired product selectivities. Furthermore, in many instances, it was not possible to satisfactorily quench the catalyst in situ and therefore purify product by distillation without first filtering the catalyst from the system. This inability to quench prior to product recovery made processing much more difficult to control and more expensive as both additional capital equipment and time would be required in recovery of the desired bis ether. The refining of alpha-alkylbenzyl ethers, such as alpha-methylbenzyl ether, by distillation, such as azeotropic distillation, has also been reported in U.S. Pat. No. 2,927,064.

In one prior process for producing alkylene oxides, e.g. propylene oxide and styrene monomer, ethylbenzene is oxidized with air in a series of oxidizers to yield a solution of ethylbenzene hydroperoxide in ethylbenzene. During this oxidation, substantial quantities of methylbenzyl alcohol and acetophenone by-products are formed. This solution of ethylbenzene hydroperoxide is then concentrated in successive steps of distillation, and unreacted ethylbenzene is recycled for oxidation. In this process, ethylbenzene hydroperoxide is then typically used to epoxidize the olefinically unsaturated compound e.g. propylene, to propylene oxide, in the presence of a suitable catalyst, and the hydroperoxide itself is converted to methylbenzyl alcohol. By-products of this reaction include additional quantities of acetophenone, phenol, benzaldehyde, 2-phenylethanol, unreacted reactants and high boiling materials.

Excess propylene in the aforementioned propylene oxide epoxidation product is normally removed by distillation and propylene oxide may then be recovered by distillation as a crude product, leaving a stream comprising excess ethylbenzene, the aforementioned by-products and residues. The stream is then distilled to recover ethylbenzene overheads, leaving an aromatic rich distilland comprising methylbenzyl alcohol, acetophenone and a variety of other by-products, including aromatic alcohols. The composition of such distilland may vary widely and comprises a variety of alcohols, ketones and other by-products, as set forth in Table I, below.

In a typical propylene-oxide styrene monomer production process, the aforementioned methylbenzyl alcohol/acetophenone distilland (bottom stream) is purified through distillation, and then is fed through styrene production reactors where it is contacted in a liquid phase with a suitable dehydration catalyst to convert methylbenzyl alcohol to styrene. After removing styrene from the dehydration reaction product by distillation, there is produced an acetophenone-rich bottoms product which is then hydrogenated using a suitable catalyst to convert acetophenone to methylbenzyl alcohol, which may then be recycled for styrene production or employed in alternative applications. Further information concerning the production of alpha-methylbenzyl alcohol from such processes is described in U.S. Pat. No. 3,403,193.

Accordingly, it is the object of the present invention to provide a novel process for the preparation of bis(alpha-alkylbenzyl) ethers.

Another object of this invention is to provide a process for the preparation of bis(alpha-alkylbenzyl) ethers from alpha-alkylbenzyl alcohols by employing a catalyst which provides high reproducibility and selectivity to the desired ether.

Still another object of the present invention is to provide a process employing an acid catalyst which need not be removed from the reaction product system prior to recovery of the ether product, thereby permitting production of the desired ether without employment of additional and expensive capital equipment.

Yet another object of the present invention involves the preparation of alpha-methylbenzyl ether from a crude methylbenzyl alcohol-containing stream obtained in olefin oxide-styrene monomer production processes.

These and other objects of the present invention will become apparent from the following more detailed description and appended claims.

SUMMARY OF THE INVENTION

In accordance with the invention, bis(alpha-alkylbenzyl) ethers are produced by reacting an alpha-alkylbenzyl alcohol in the presence of an acidic clay catalyst of specified characteristics under conditions which form a reaction product containing, in high yield, the desired bis(alpha-alkylbenzyl) ether. Major features characteristic of the process of the present invention include the employment of commercially available acid clay catalyst at low concentration; catalyst addition to the alpha alkylbenzyl alcohol reactant at ambient temperature, thereby permitting ready control of obtainable reaction products; quenching of the catalyst upon completion of the reaction, thereby precluding decomposition of desired bis ether product; high conversions of alcohol reactant over short reaction times while maintaining high selectivity to desired bis ether product; capability of recovery of desired bis ether product by vacuum distillation in the presence of the quenched catalyst; and excellent reproducibility in the obtainment of desired results.

In accordance with one specific embodiment, commercially available technical grade, alpha-alkylbenzyl alcohols, such as methylbenzyl alcohol, are etherified in the presence of acid clay catalysts to provide, in high yield commercially acceptable bis(alpha-alkylbenzyl) ethers.

In another specific embodiment, methylbenzyl alcohol present in a crude stream obtained from an olefin oxide/styrene monomer process, admixed with acetophenone, 2-phenylethanol, and a variety of other aromatic hydrocarbons and oxygenated derivatives thereof, is contacted with an acidic clay catalyst under conditions which provide a high yield of bis(alpha-methylbenzyl) ether.

The ethers produced by the process of the present invention find particular use as dielectric fluids for capacitors and carbonless carbon paper solvents.

DETAILED DESCRIPTION OF THE INVENTION

The process of this invention is applicable to the production of bis(alpha-alkylbenzyl) ethers by etherification of alpha-alkylbenzyl alcohols. In general, the bis(alpha-alkylbenzyl) ethers capable of production in accordance with the process of the present invention correspond to the formula:

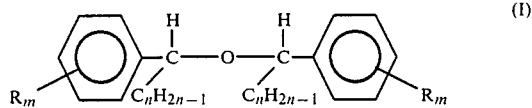

wherein R is the same or different lower alkyl of 1 to 6 carbon atoms, lower haloalkyl, bromo, chloro, sulfo or nitro; m is an integer not greater than 3 and n is an integer of from 1 to 7, inclusive. The desired ethers of the present invention are obtained by heating an alpha alkylbenzyl alcohol of the formula:

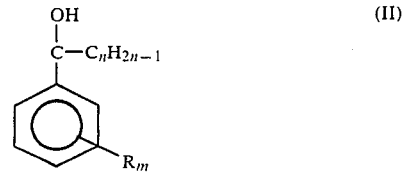

wherein R, m and n are as defined above. Exemplary of the alpha alkylbenzyl alcohols which are employed in preparing the desired ethers by the process of the present invention include, but are not limited to:

alpha-methylbenzyl alcohol
alpha-ethylbenzyl alcohol
alpha-(4-chloro-phenyl)-ethanol
alpha-(3,4,5-tribromo-phenyl)-ethanol
alpha-(4-chloromethyl-phenyl)-ethanol
alpha-(4-nitro-phenyl)-ethanol
alpha-pentylbenzyl alcohol
alpha-(4-bromo-phenyl)-hexanol
alpha-(4-sulfo-phenyl)-ethanol
alpha-(4-trifluoromethylphenyl)-ethanol
alpha-hexylbenzyl alcohol
alpha-propylbenzyl alcohol
and the like, and mixtures thereof.

In producing the bis(alpha-alkylbenzyl) ethers in accordance with the process of the present invention, the alpha-alkylbenzyl alcohol described is heated with agitation at a temperature below about 200° C., generally between about 125° C. and 175° C., and preferably between about 125° C. and 150° C. in the presence of an acidic clay catalyst having a surface area of at least about 100 square meters per gram, for a time sufficient to effect conversion of at least about 75% of said alcohol to the desired ether, thereby forming a reaction product mixture.

The etherification reaction may be carried out in the presence or absence of an inert solvent, such as an aromatic solvent, illustratively, benzene, toluene, acetophenone, or xylene.

As is above indicated, it is not necessary that the alpha-alkylbenzyl alcohol employed in the process of the present invention be a pure material. In this connection, an alternative embodiment of the invention resides in the use of an aromatic rich distilland comprising alpha-methylbenzyl alcohol, acetophenone and a variety of other by-products, including alcohols and ketones and other by-products obtained from the olefin oxide-styrene production process. The composition of a typical etherification feed obtained from the propylene oxide/styrene coproduction process is set forth in Table I below:

TABLE I

| Component | Weight (%) |
|---|---|
| alpha-phenylethanol | 75–85 |
| acetophenone | 10–20 |
| 2-phenylethanol | <5 |
| benzyl alcohol | <2 |
| benzaldehyde | <1 |
| cumylalcohol | <1 |
| phenol | <1 |
| cumene | <1 |
| ethylbenzene | <1 |

Water formed during the etherification reaction is removed as formed by distillation, or as an azeotropic mixture with the solvent, if employed, and if desired, its removal may be facilitated in conventional manner by the additional introduction of an inert gas, such as nitrogen, into the reaction system.

The catalysts employed in the process of the present invention are acidic clays characterized by having a surface area of at least about 100 square meters per gram, preferably at least about 200 and more square meters per gram. Any clay having a residual acidity of at least 1 milligram, preferably at least about 5 milligrams, potassium hydroxide per gram of clay, as determined by ASTM D-1613, may be employed as the catalyst in the process of the present invention. In general, clays composed of attapulgite and montmorillonite are capable of serving as catalysts or catalyst precursors herein. Typically, clay materials used widely in decolorization and oil refining applications which have been acidified in conventional manner have been found to be adapted for use in the process of the present invention. Suitable processes for acid activation of clays is described in U.S. Pat. Nos. 2,671,058; 2,563,977; and 4,325,847, the disclosures of which are hereby incorporated herein by reference. The acidic clay catalyst is generally employed as a fine powder in the process of the invention in quantities ranging from about 0.05 to 5, preferably from about 0.1 to about 0.5, percent, by weight, of the alpha alkylbenzyl alcohol starting material employed in the process.

In accordance with the process of the present invention, the etherification reaction is effected for a time sufficient, generally about 15 minutes to 4 hours, to effect conversion of at least about 75% of the alcohol reactant thereby forming a reaction product mixture. Following completion of the reaction, a basic compound is introduced into the reaction product mixture to deactivate the catalyst, i.e. convert the catalyst to an inert compound. If desired, the catalyst may be removed by conventional separating procedures, as by filtration, prior to recovery of the desired product. However, a further feature of the present invention resides in capability of recovery and/or purification of the desired bis ether by vacuum distillation in the presence of the deactivated catalyst, thereby eliminating the need for additional capital equipment and power input, generally required in connection with use of conventionally employed acid catalysts. Any basic compound capable of neutralizing acidity of the catalyst may be employed. Illustrative suitable compounds employable for this purpose include alkali and alkaline earth metal hydroxides, carbonates or bicarbonates such as sodium hydroxide, sodium carbonate or sodium bicarbonate. Alternatively, ammonium or ammonium hydroxides or other salts, as well as organic amines such as alkyl amines, illustratively, triethylamine, may be employed for this purpose. It is critical, however, to employ the basic agent in slight excess of the amount sufficient to neutralize i.e. be just above equivalence in acidity, the catalyst. Neutralization of the catalyst prevents decomposition of the desired ether product.

A variety of conventional methods, including distillation, extraction, or physical phase separation may be employed to recover the desired ether reaction product, unreacted starting materials, by-products, impurities, catalysts and diluents, if employed. In general, lower boiling unreacted starting materials are initially removed in a forecut, by distillation, followed by distillation of the desired ether product, which is carried out generally under vacuum.

The process of the present invention may be illustrated by the following examples. All parts and percents are based on weight. The reaction ratio and selectivities are calculated from analysis by Gas Chromotography.

This example describes the general experimental procedure used herein to produce bis(alpha-methylbenzyl) ether from pure alpha-methylbenzyl alcohol or a crude mixture, obtained from the propylene oxide/styrene process comprised described above, of 76.23 percent methylbenzyl alcohol 18.72 percent acetophenone, and 5.05 percent of other components described in Table I, above.

Into a 250 ml flask equipped with an agitator, a thermometer and a Dean-Stark condenser having a water-measuring tube, there were charged 100 parts of pure or crude alphamethylbenzyl alcohol, as described, in each of a series of experiments. Thereafter, the indicated quantity of catalyst listed in following Table II was added thereto with stirring at ambient temperature and the mixture was heated at the temperatures for the periods indicated. In the case of Examples 1–5, inclusive, the catalyst was filtered and removed before recovery of the bis(alpha-methylbenzyl) ether from the reaction product mixture and, in the case of Examples 6 and 7, the catalyst was quenched upon completion of the 30 minute reaction time with a 29 weight percent aqueous potassium hydroxide solution, but retained in the reaction mixture during subsequent recovery. Thereafter, the desired bis(alpha-methylbenzyl) ether was recovered from the reaction mixtures of each Example by distillation at a temperature of 115°–122°/1torr., following removal of unreacted methylbenzyl alcohol and styrene in a forecut at 75°–110°/1torr. The results are set forth in Table II, below.

TABLE II

Synthesis of Bis(α-methylbenzyl) Ether (BAMBE)

| | | | | Reaction Time, 30 min. | | | | Reaction Time, 60 min. | | | |
|---|---|---|---|---|---|---|---|---|---|---|---|
| | | | | Conversion | | Selectivity mol % | | Conversion | | Selectivity mol % | |
| Example | Feed | Catalyst | Temp. °C. | mol % | Styrene | BAMBE | Others | mol % | Styrene | BAMBE | Others |
| 1 | P(1) | Amberlyst ® 15(3) | 110–120 | 75.82 | 23.08 | 69.24 | 7.68 | — | — | — | — |
| 2 | C(2) | Amberlyst ® 15(3) | 115–127 | 76.28 | 32.56 | 63.44 | 4.0 | 99.52 | 25.0 | 0.8 | 74.2 |
| 3 | P(1) | Filtrol ® 20(4) | 128–140 | 81.04 | 1.4 | 96.5 | 2.1 | 92.3 | 5.4 | 52.6 | 42.0 |
| 4 | P(1) | Filtrol ® 13(5) | 130–140 | 65.68 | 0.8 | 99.2 | — | 92.4 | 6.3 | 70.6 | 23.1 |
| 5 | C(2) | Filtrol ® 13(5) | 135–150 | 86.70 | 3.9 | 96.1 | — | 89.4 | 5.7 | 77.1 | 17.2 |
| 6 | C(2) | Filtrol ® 13(5) (6) | 135–150 | 87.50 | 8.2 | 95.3 | — | 87.5 | 7.7 | 92.3 | |

TABLE II-continued

| | | | | Synthesis of Bis(α-methylbenzyl) Ether (BAMBE) | | | | | | |
|---|---|---|---|---|---|---|---|---|---|---|
| | | | | Reaction Time, 30 min. | | | | Reaction Time, 60 min. | | |
| Example | Feed | Catalyst | Temp. °C. | Conversion mol % | Styrene | Selectivity mol % BAMBE | Others | Conversion mol % | Styrene | Selectivity mol % BAMBE | Others |
| 7 | C[(2)] | Filtrol ® 13[(5) (6)] | 135-150 | 85.74 | 5.6 | 94.4 | — | 89.9 | 6.7 | 93.2 | — |

[(1)]P = Pure Commercial Methyl Benzyl Alcohol. (98.5 wt %.)
[(2)]C = Crude Methyl Benzyl Alcohol. comprised of 76.23 wt % MBA, 18.72 wt % Acetophenone. 5.05 wt % others
[(3)]A polystyrene-based heterogeneous sulfonic acid resin catalyst supplied by Rohm & Haas Company, charged in an amount of 1.0 percent of MBA present
[(4)]An activated clay having a surface area of 285 square meters per gram and a residual acidity of 12 mg. KOH per gram, supplied by the Filtrol Corporation, charged in an amount of 0.2 percent of MBA present.
[(5)]An acid treated clay having a surface area of 325 square meters per gram and a residual acidity of 16 mg. of KOH per gram, supplied by the Filtrol Corporation, charged in an amount of 0.2 percent of MBA present.
[(6)] Catalyst quenched at 30 minute reaction time with 25 wt % of KOH, based on the weight of catalyst clay employed (on a dry basis).

As is noted from Table II, high purity bis(alpha-methylbenzyl) ether is produced with little decomposition in accordance with Examples 6 and 7, illustrative of the process of the present invention; the product ether produced in these Examples was substantially odorless, and of high quality. As is further evident from the results set forth above, use of the Amberlyst catalsyt and failure to quench the Filtrol catalysts in the process results in a number of drawbacks, including high selectivity to undesired styrene and conversion of the ether, once formed, to undesirable by-products.

What is claimed is:

1. Process for the production of bis(alpha-alkylbenzyl) ethers corresponding to the formula:

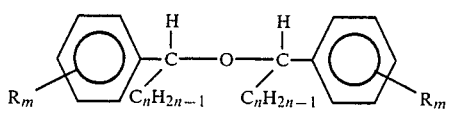

wherein, R is a member selected from the group consisting of lower alkyl, lower haloalkyl, chloro, bromo, sulfo and nitro radicals; m is an integer not greater that 3 and n is an integer of from 1 to 7, inclusive, comprising:

(a) heating, while removing water of dehydration as formed, an alpha alkylbenzyl alcohol of the formula:

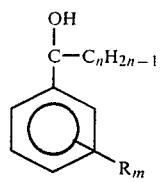

wherein, R, m and n are as defined above, with agitation, at a temperature below about 200° C. in the presence of an acidic clay present in catalytic amount and having a surface area of at least about 200 square meters per gram, and an acidity of at least 1 milligram potassium hydroxide per gram of clay for a time sufficient to effect conversion of at least about 75% of at said alcohol to the desired ether and thereby forming a reaction product mixture;

(b) introducing a basic compound to the reaction product mixture of Step (a), above, in an amount sufficient to deactivate the catalyst; and (c) recovering the desired bis(alpha-alkylbenzyl) ether from the reaction product mixture.

2. The process of claim 1 wherein said clay is present in an amount of between 0.05% and 5%, by weight, of said alcohol.

3. The process of claim 1 wherein said heating is carried out at a temperature of between about 125° C. and 150° C.

4. The process of claim 1 wherein heating of the alpha-alkylbenzyl alcohol is effected in an inert solvent.

5. The process of claim 2 wherein m is 0 and n is 1 in each of said formulas.

6. The process of claim 5 wherein said clay has a surface area of at least about 250 square meters per gram and an acidity of at least about 5 milligrams potassium hydroxide per gram of clay.

7. The process of claim 2 wherein the alpha methyl benzyl alcohol starting material is present, in major proportion, as a component of an aromatic rich distilland product mixture derived from the ethyl benzene hydroperoxide epoxidation of an olefinically unsaturated compound.

8. The process of claim 6 wherein the ether is recovered by subjecting the reaction product mixture to distillation in the presence of the clay.

9. In the process for the production of bis(alpha-methylbenzyl) ether by heating an alpha methylbenzyl alcohol reactant in the presence of an acid catalyst at an elevated temperature, followed by deactivation of the acidic catalyst by contact with a basic compound, and recovery of the desired ether, the improvement which comprises:

(a) employing, as reactant, an aromatic-rich distilland product mixture containing alpha-methylbenzyl alcohol in major proportion and, obtained from the ethyl benzene hydroperoxide epoxidation of an olefinically unsaturated compound, (b) employing as said catalyst, an acidic clay having a surface area of at least about 200 square meters per gram, and an acidity of at least 1 milligram potassium hydroxide per gram of clay (c) heating of the mixture containing alpha-methylbenzyl alcohol is effected at a temperature of between about 125° C. and 175° C. for a time sufficient to effect conversion of at least about 75% of the alpha methylbenzyl alcohol contained in said mixture to the desired bis(alpha-methylbenzyl) ether, (d) recovering said bis(alpha-methylbenzyl) ether by distillation following removal of unreacted methyl benzyl alcohol and lower boiling impurities.

10. The process of claim 9 wherein said clay has a surface area of at least about 250 square meters per gram and an acidity of at least about 5 milligrams potassium hydroxide per gram of clay.

11. The process of claim 9 wherein the distillation of step (d) is effected in the presence of the quenched clay catalyst.

* * * * *